United States Patent [19]
Tibbling et al.

[11] Patent Number: 5,412,441
[45] Date of Patent: May 2, 1995

[54] KERATOMETER DEVICE HAVING PHOTOGRAPHICALLY PRODUCED BORE PATTERN

[76] Inventors: Lars Tibbling, RR3 952-A, Highland Lakes, Vernon Township, N.J. 07422; Roy Maus, 2305 Garfield St., North Bellmore, N.Y. 11710

[21] Appl. No.: 206,948
[22] Filed: Mar. 7, 1994
[51] Int. Cl.⁶ ............................................. A61B 3/00
[52] U.S. Cl. ................................... 351/200; 351/221; 351/246
[58] Field of Search ............... 351/200, 211, 212, 247, 351/221, 206, 246

[56] References Cited

U.S. PATENT DOCUMENTS

| | | | |
|---|---|---|---|
| 3,181,351 | 5/1965 | Stauffer | 351/200 |
| 3,639,043 | 2/1972 | Townsley | 351/212 |
| 4,426,141 | 1/1984 | Holcomb | 351/212 |
| 4,772,115 | 9/1988 | Gersten et al. | 351/212 |
| 4,863,260 | 9/1989 | Gersten et al. | 351/212 |
| 5,018,850 | 5/1991 | Gersten et al. | 351/212 |

*Primary Examiner*—William L. Sikes
*Assistant Examiner*—Huy Mai
*Attorney, Agent, or Firm*—Howard R. Popper

[57] ABSTRACT

An improved conical keratometer wherein the parent image of the pattern to be reflected upon a target positioned adjacent to the illuminated bore is recorded on a film slide retained within the keratometer bore. Opposite edges of the slide are chamfered at equal but opposite angles so that, when the spindeled slide is released, the chamfered edges will meet along a line of contact rather than butting squarely together. The film slide is rolled so that the emulsion side is toward the periphery of the cone bore and the chamfering allows that side to lie smoothly against the cone bore without any gaps so that an undistorted image may reliably be reflected upon a standard target.

10 Claims, 3 Drawing Sheets

KERATOMETER DEVICE HAVING PHOTOGRAPHICALLY PRODUCED BORE PATTERN

FIELD OF THE INVENTION

This invention relates generally to Placido disk keratometers and, more particularly, to an improved keratometer of the conical type such as disclosed in Gersten et al U.S. Pat. No. 5,018,850.

BACKGROUND OF THE INVENTION

Mapping the topography of the human cornea is facilitated by employing a Placido disk device which causes a predetermined pattern of illuminated rings to be reflected upon the cornea. While the conventional Placido disk fairly easily produces rings in the apical region of the cornea, to provide rings in the limbal region of the cornea it has until recently been necessary to employ a rather large diameter Placido disk. However, U.S. Pat. No. 4,772,115 disclosed a compact Placido disk device which provides a greater number of limbal rings without incurring the penalty of a large and bulky apparatus. Briefly, the device of that patent employed a conical structure made of light pervious plastic having an eye-port at one end of a substantially cylindrical central bore. The base of the cone was illuminated and a series of light-transmitting and opaque bands were arrayed along the central bore. The series of light transmitting and opaque bands were produced by first coating the central bore with a uniform opaque coating and then making a series of ring-shaped cuts through the coating to reveal the underlying light transmitting plastic material of the cone. The bore was illuminated by a lightbox attached to the base of the conical structure. While that device permitted the large and bulky Placido disk to be replaced by a more compact device that reflected an acceptable number of illuminated rings upon both the apical and limbal regions of the cornea, certain difficulties were encountered in its fabrication. A further improvement in the conical format keratometer was disclosed in U.S. Pat. No. 5,018,850 in which the light and dark bands for the illuminated bore were produced by first incising bands along the bore, filling the incised bands with opaque material and thereafter removing the excess opaque material from the lands. The latter method permitted a more accurate delineation of the edges of the opaque rings.

While the Placido disk devices fabricated according to the foregoing methods have been successfully employed in practice, the need to employ precise, multistep machine processing steps in both fabrication techniques has been found to be expensive and time consuming. A more economical method of producing a precisely defined illuminated pattern on the cornea would be desirable. In addition, it would be most advantageous to be able to cause other precisely defined illuminated patterns to be reflected upon the cornea such as, for example, radial lines as well as non-circular mire patterns.

SUMMARY OF THE INVENTION

In accordance with the principles of my invention, in one illustrative embodiment thereof, instead of incising the pattern of light and dark bands within the bore of the conical keratometer, the pattern to be reflected from the cornea is provided by a film slide upon which is recorded the parent image of the image to be reflected, the film slide being retained within the bore of the keratometer and illuminated through the transparent base of the keratometer. The film slide may bear the photographic image of any precisely drawn pattern. For example, a series of spaced-apart, ruled, opaque and white stripes may be drawn and then photographed. The photographic film is then developed and a positive photographic slide bearing the image of the ruled stripes made on polyester-backed material is made. The film slide is cropped so that its width equals the perimeter of the keratometer cone bore. The slide is then coiled or spindeled and inserted into the cone bore. When allowed to unwind, the film slide is retained within the bore. Advantageously, the cone may be heated slightly before the film slide is inserted so that the cone will shrink about the film slide making retention thereof more secure. Two opposite edges of the slide are advantageously chamfered at equal but opposite angles so that, when the spindeled slide is released, the chamfered edges will meet along a line of contact rather than butting squarely together. The film slide is rolled so that the emulsion side is toward the periphery of the cone bore and the chamfering allows that side to lie smoothly against the cone bore without any gaps or "bubbles". Having the emulsion side in contact with the keratometer cone bore not only protects the photographic image from scratches, etc., but also assures that the image reflected upon a standard target will not be distorted when the cone is illuminated. Accordingly, a known image can be mass produced and reliably reflected upon the target. When the keratometer cone is illuminated (advantageously by a light source positioned at the base of the cone) the stripes on the film slide are reflected as concentric circles on a spherical target such as a polished steel ball which simulates the cornea of a human eye positioned at the a apex eye-port of the keratometer.

GENERAL DESCRIPTION

Figure 1:
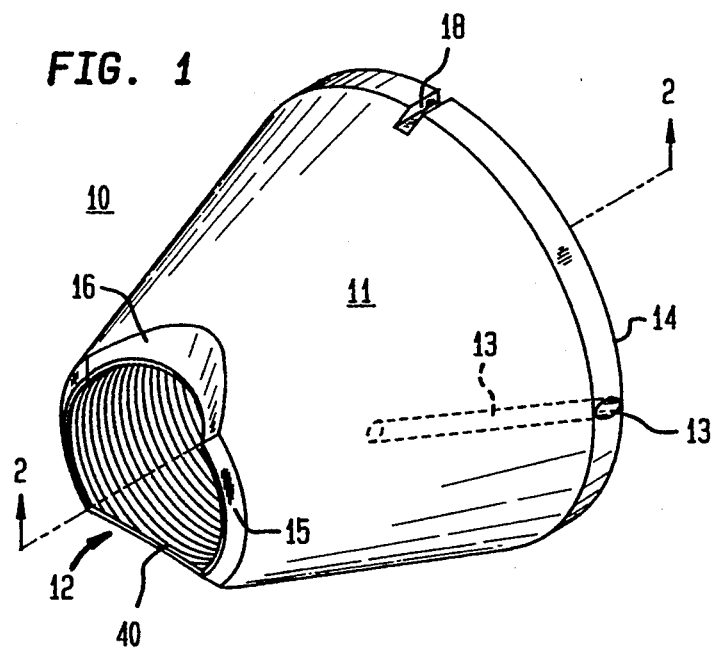
FIG. 1 is a three-quarters frontal view of the keratometer cone with the pattern-bearing photographic slide retained within its bore.

Referring now to FIG. 1 a three-quarter frontal view of the keratometer cone 10 is shown, rotated so that its underside is uppermost. The cone is advantageously made of transparent, clear acrylic plastic and has a substantially cylindrical central bore 12. As shown in U.S. Pat. No. 4,863,260, the outer surface of cone 10 tapers from its base 14 toward the eye-port 15 at its apex. As shown in application Ser. No. 07/623,720 filed Jul. 24, 1992 entitled "Compact Keratoscope with Interchangeable Cones", a pair of tunnels 13 (shown more clearly in the sectional view, FIG. 2), are advantageously provided through the walls of the cone to accommodate a pair of laser beams (not shown) which intersect at eye-port 15 for accurately determining the precise position of the patient's cornea. The upper edge 16 and the lower edge 17 (see FIG. 3) of cone 10 are chamfered adjacent to eye-port 15 to accommodate the eyebrow and cheekbone of the patient's eye. Also, as disclosed in the aforementioned patent application, the base 14 of the cone is provided with a locating notch 18 and the base is illuminated by a light source (not shown). The outer surface of cone 10 is provided with a coating 11 to redirect the light from base 14 toward the central bore 12.

Figure 2:
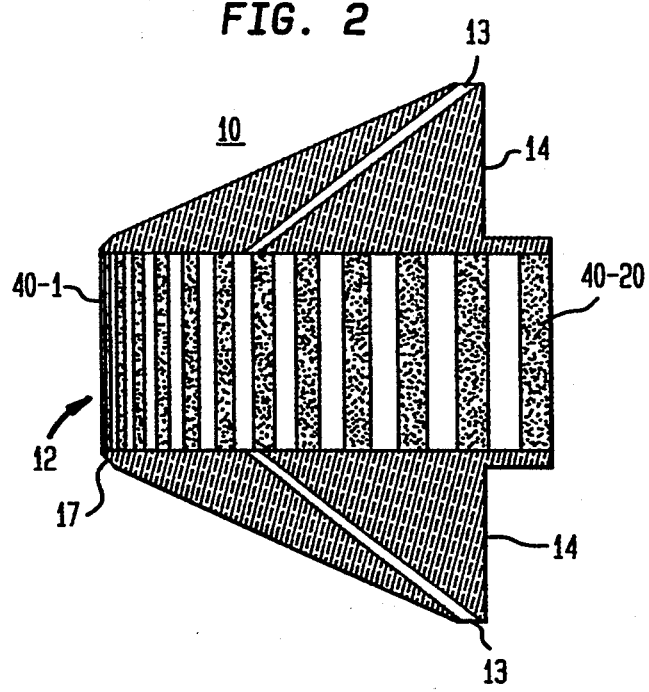
FIG. 2 is a cross-sectional view through the keratometer cone.
Figure 3:
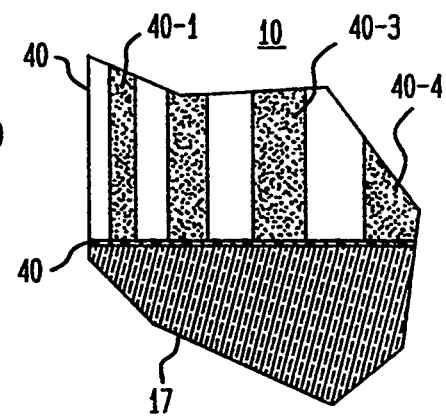
FIG. 3 is an enlarged cross-sectional view showing details of the front portion of the keratometer cone.

Visible at the left-hand end of bore 12 at the eye-port 15 of cone 10 is film slide 40 with its series of opaque and light-transmitting bands 40-1 through 40-20 (shown more clearly in the crossectional views of FIGS. 2 and 3. In FIG. 2, the film slide 40 of FIG. 4 has been spindeled, inserted into the central bore 12 of cone 10, and allowed to unwind so that its emulsion side 53 (see FIG. 5) closely conforms to the geometry of bore 12. Prior to inserting the spindeled film slide 40 into bore 12, cone 10 is advantageously gently heated to expand the diameter of bore 12 beyond its room temperature dimension so that upon cooling bore 12 will shrink about the periphery of the rolled film slide and securely retain it. Heating the acrylic plastic of cone 10 to approximately 130° F. is found to be sufficient to expand bore 12 so that when cone 10 cools the film slide 40 will securely be retained in place.

FIG. 3 is an enlarged detail view of the eye-port 15 end of cone 10 showing the chamfer 17 which accommodates the cheekbone of the patient thereby allowing the patient's cornea to be more comfortably positioned. In addition, the first through fourth opaque stripes of film strip 40 are shown at 40-1 through 40-4.

Figure 4:
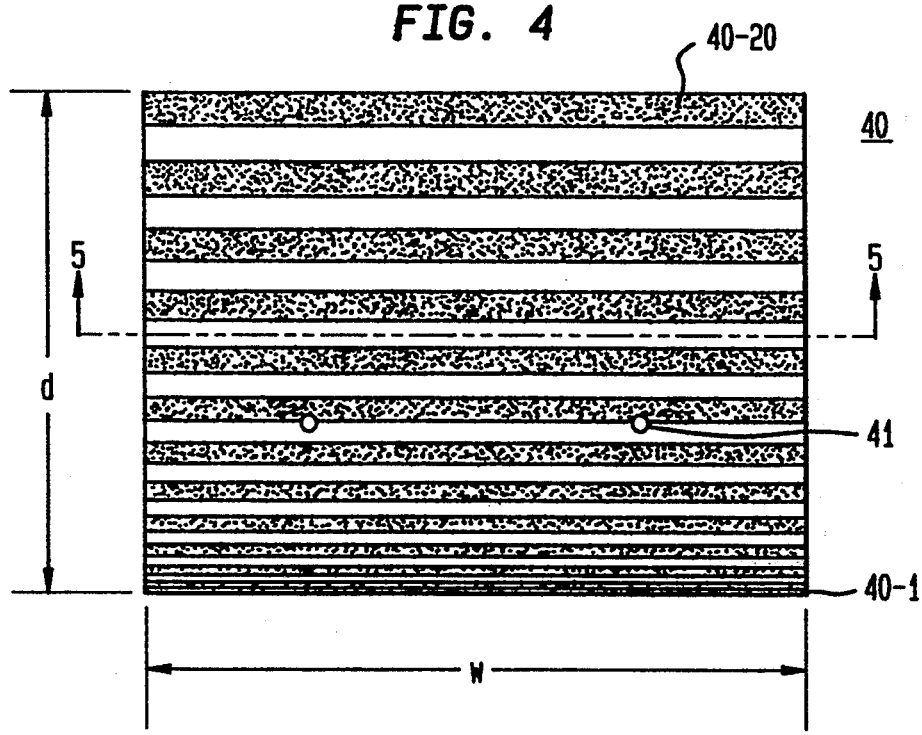
FIG. 4 is a plan view of the photographic slide before it is spindeled.

Referring now to FIG. 4, a plan view of film slide 40 is shown bearing a plurality of spaced-apart opaque stripes 40-1 through 40-20 which are the photographic image of a previously drawn pattern (not shown). If the drawn pattern is of ruled opaque, parallel lines and the photographic image is rolled into a cylinder, the image that will be reflected from a perfectly spherical specular surface, such as a steel ball, will be a series of concentric rings or bands. The spacing of the ruled lines is advantageously chosen so that when the photographic image of the ruled lines is reflected from a perfectly spherical specular target surface the concentric rings will be evenly spaced. It should be noted, of course, that to project a series of evenly spaced rings on a spherical object such as a cornea, the bands 40-1 through 4-20 on photographic film strip 40 will, in general, not be equally spaced.

Illustrative specifications for film slide 40 are as follows:

| Material: DuPont "Cronar" brand Rapid Contact Film | |
| --- | --- |
| Width W | 100. mm. |
| Depth d | 55. mm. |
| Last opaque strip width | 6.2 mm |
| First opaque strip width | 0.5 mm. |
| Number of opaque strips | 20. |
| Slide thickness | 0.080 mm |
| Edge taper t | 5.0 degrees |

Holes 41, FIG. 4, are advantageously punched through film slide 40 so as to be in registration with the exit points of the transverse tunnels 13 when slide 40 is positioned within bore 12 of the keratometer cone.

Figure 5:
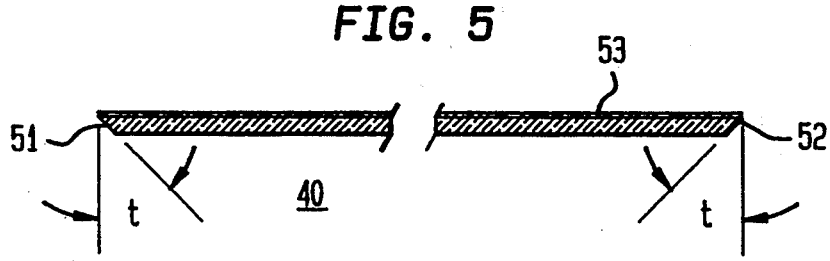
FIG. 5 is an enlarged edge view of the photographic slide showing its chamfered edges.
Figure 6:
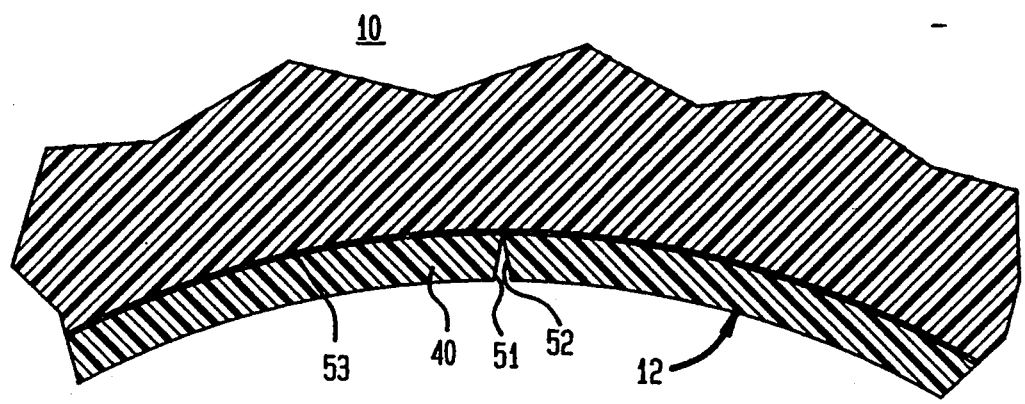
FIG. 6 is an enlarged, end-view of the keratometer bore with the chamfered film slide correctly installed.
Figure 7:
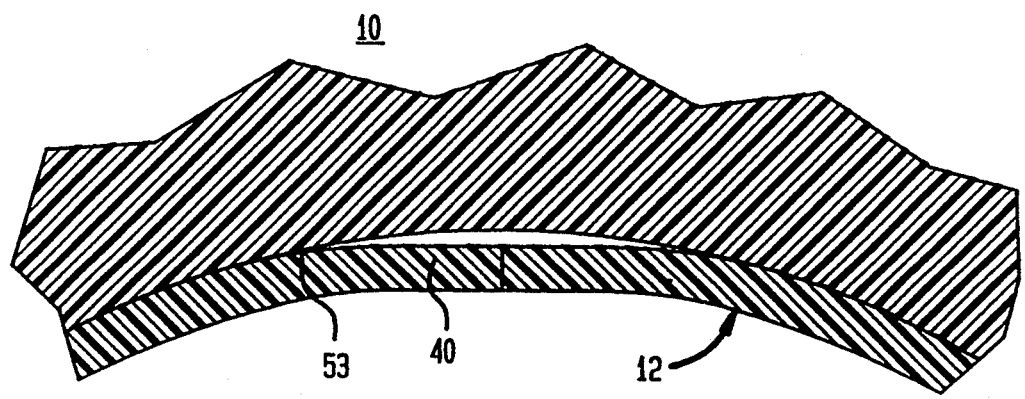
FIG. 7 is an enlarged, end-view of the keratometer bore showing the effect of installing an unchamfered film slide.

As shown in FIG. 5, the opposite edges 51, 52 of film 40 are shaved to have a taper t of approximately 5 degrees. When film slide 40 is spindeled so that emulsion side 53 is on its outer periphery, opposite edges 51, 52 will come together along a line of contact, as shown in FIG. 6. Had edges 51, 52 been allowed to remain square, as shown in FIG. 7, the edges would butt together squarely but, unfortunately, the outer periphery of the film strip would then pull away from the surface of the cone bore 12. Chamfering each of edges 51, 52 by equal but opposite angles t allows the emulsion surface of slide 40 to lie smoothly against the surface of bore 12.

What has been described is deemed to be illustrative of the principles of my invention. Thus, while I have shown a pattern of opaque and light transmitting bands 40-1 through 40-20, a greater or lesser number of such bands may be used. And while the bands are shown in FIG. 4 as all being parallel to one another (and therefore orthogonal to the axis of bore 12 when film 40 is rolled-up), it should be apparent that other orientations of the bands may be provided. For example, some of the photographed bands may be at right angles to the bands shown in FIG. 4 so as to reflect on a target a pattern of illuminated and dark bands that are parallel to the axis of bore 12. Further and other modifications to the photographic image may be made by those skilled in the art to reflect other desired patterns on a target without departing from the spirit and scope of my invention.

What is claimed is:

1. A keratometer having a transparent, substantially cylindrical bore of plastic material, said bore being capable of being illuminated, a photographic film slide having recorded thereon a predetermined pattern, said film slide being spindeled and retained within and illuminated from said bore.

2. A keratometer according to claim 1 wherein said film slide is of polyester material.

3. A keratometer according to claim 2 wherein said bore is shrunk-fit about said film slide.

4. A keratometer according to claim 1 wherein opposite edges of said spindeled slide are chamfered, said edges being in line contact with each other within said bore.

5. A keratometer according to claim 4 wherein said film slide has an emulsion side and said emulsion side is in contact with the periphery of said bore.

6. A keratometer according to claim 1 wherein said film slide bears the photographic image of ruled lines.

7. The method of making a conical keratometer comprising the steps of:
 a. heating a body of transparent plastic material having a bore to expand the diameter of said bore;
 b. inserting a coiled film strip in said bore, said film strip bearing the parent image of a pattern to be reflected on a target positioned adjacent to said bore, said film strip having a perimeter substantially equal to the perimeter of said bore when cool;
 c. allowing said film strip to unwind within said bore; and
 d. allowing said heated cylindrical bore to cool and shrink about said coiled film strip.

8. The method of claim 7 wherein opposite edges of said film strip are chamfered before said strip is coiled.

9. The method of claim 7 wherein said film strip is a photographic slide bearing the recorded image of an illuminable pattern.

10. The method of claim 8 wherein said film strip is of polyester backed material.

* * * * *